(12) United States Patent
Phan et al.

(10) Patent No.: US 9,180,455 B2
(45) Date of Patent: Nov. 10, 2015

(54) VENT CONFIGURATION FOR A BLOOD SAMPLER

(75) Inventors: Bao Phan, Fremont, CA (US); Martin Antoine Mathelier, Garnerville, NY (US); Hoang Quoc Chau, San Jose, CA (US); Simin Yao, Boonton Township, NJ (US); Eugene Prais, West Milford, NJ (US)

(73) Assignee: Polymer Technology Systems, Inc., Indianapolis, IN (US)

(*) Notice: Subject to any disclaimer, the term of this patent is extended or adjusted under 35 U.S.C. 154(b) by 2 days.

(21) Appl. No.: 13/587,439

(22) Filed: Aug. 16, 2012

(65) Prior Publication Data

US 2013/0216452 A1    Aug. 22, 2013

(51) Int. Cl.

| | |
|---|---|
| *B01L 3/00* | (2006.01) |
| *A61B 5/151* | (2006.01) |
| *G01N 33/49* | (2006.01) |
| *A61B 5/15* | (2006.01) |
| *G01N 1/00* | (2006.01) |
| *B01F 15/00* | (2006.01) |
| *G01N 1/38* | (2006.01) |
| *B01F 15/02* | (2006.01) |
| *A61J 1/20* | (2006.01) |

(52) U.S. Cl.
CPC .............. *B01L 3/508* (2013.01); *A61B 5/1411* (2013.01); *A61B 5/150022* (2013.01); *A61B 5/15142* (2013.01); *A61B 5/150213* (2013.01); *A61B 5/150259* (2013.01); *A61B 5/150343* (2013.01); *A61B 5/150755* (2013.01); *B01F 15/00512* (2013.01); *B01F 15/0206* (2013.01); *B01L 3/502* (2013.01); *G01N 1/38* (2013.01); *B01L 3/5082* (2013.01); *B01L 3/502715* (2013.01); *B01L 3/502723* (2013.01); *B01L 2200/027* (2013.01); *B01L 2200/0684* (2013.01); *B01L 2200/0689* (2013.01); *B01L 2200/087* (2013.01); *B01L 2300/042* (2013.01); *B01L 2300/047* (2013.01); *B01L 2300/048* (2013.01); *B01L 2400/0478* (2013.01); *B01L 2400/0481* (2013.01); *B01L 2400/0683* (2013.01); *G01N 33/49* (2013.01)

(58) Field of Classification Search
USPC .......... 422/63, 68.1, 100, 500, 512, 546, 550, 422/547, 560–561; 73/864.02; 600/576, 600/580
See application file for complete search history.

(56) References Cited

U.S. PATENT DOCUMENTS 4,411,163 A * 10/1983 White ....................... 73/864.02
4,653,512 A *  3/1987 Losada ..................... 600/576

(Continued)

FOREIGN PATENT DOCUMENTS

WO    2011029184 A1    3/2011

OTHER PUBLICATIONS

International Search Report and Written Opinion for Application No. PCT/US2012/051125 dated Dec. 10, 2012.

*Primary Examiner* — Jennifer Wecker

(74) *Attorney, Agent, or Firm* — Haynes and Boone, LLP

(57) ABSTRACT

A blood sampler device includes a blood collector and a sampler body. The blood collector is designed to collect a sample of a fluid, such as blood, from a user and to be inserted into the sampler body, such that the collected blood can be discharged into a liquid chamber in the sampler body to mix with a liquid stored in the liquid chamber for testing. The blood collector includes vents that are designed to facilitate the flow of air out of the liquid chamber during this insertion, such that a lower and more consistent pressurization can be achieved within the liquid chamber. This design may also increase user comfort and enhance the accuracy of testing performed on the collected fluid.

23 Claims, 11 Drawing Sheets

(56) References Cited

U.S. PATENT DOCUMENTS

| | | |
|---|---|---|
| 7,749,770 B2 | 7/2010 | Nguyen et al. |
| 7,771,655 B2 * | 8/2010 | Ramel ............................ 422/63 |
| 8,251,500 B2 * | 8/2012 | Yamada et al. ................. 347/86 |
| 2005/0196872 A1 * | 9/2005 | Nguyen et al. ................. 436/174 |
| 2011/0212482 A1 * | 9/2011 | Jangam et al. .................. 435/29 |
| 2013/0060162 A1 * | 3/2013 | Crawford et al. ............. 600/576 |

\* cited by examiner

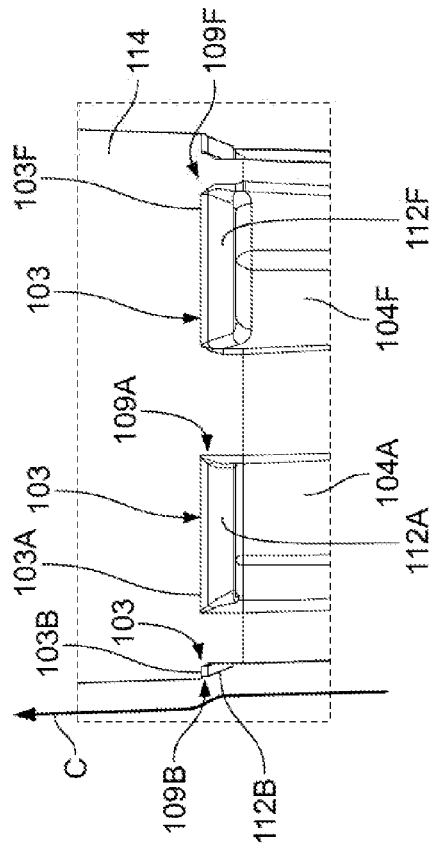
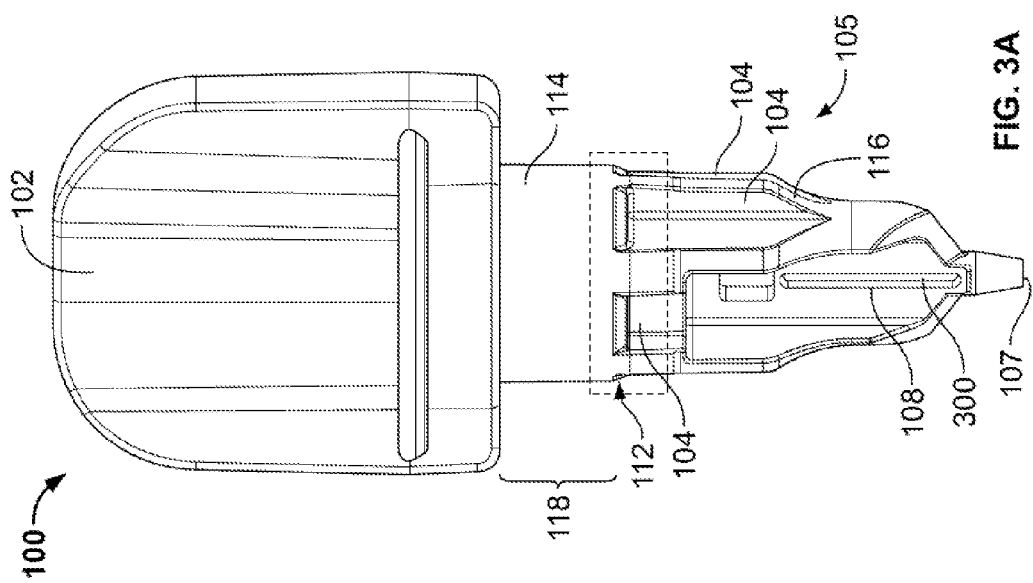
FIG. 3B
FIG. 3A

VENT CONFIGURATION FOR A BLOOD SAMPLER

CROSS-REFERENCE TO RELATED APPLICATION

The present application claims the benefit of the filing date of U.S. Provisional Patent Application No. 61/524,141 filed Aug. 16, 2011, the disclosure of which is hereby incorporated herein by reference.

TECHNICAL FIELD

The present invention relates to mechanical devices for mixing a fluid sample with a treatment solution. Preferably, the fluid sample is a blood sample and the treatment solution is a buffer or dilutent.

BACKGROUND OF THE INVENTION

U.S. Pat. No. 7,588,724 (application Ser. No. 11/043,510) and U.S. Pat. No. 7,749,770 (application Ser. No. 12/462,810), and U.S. Pat. No. 7,771,655 ("the '655 patent") (application Ser. No. 11/485,743), all entitled "Mechanical Device For Mixing A Fluid Sample With A Treatment Solution," the disclosures of which are all hereby incorporated herein by reference, describe two part devices for mixing a blood sample with a treatment solution prior to release of the treated sample into a fluid analyte meter. Although very useful, a disadvantage of these systems is that, despite the disclosed features, it can be difficult to control pressurization in the devices such that a correct sample volume is delivered to the test cartridge.

For example, these known blood sampler devices often cause a sudden change in the resistance force profile felt by a user while inserting a blood collector into a sampler body, known as the "double pop" sensation. This sudden change, or "jump," in the resistance force felt by a user often causes users to prematurely stop inserting the blood collector into the sampler body in such known devices, which can result in a lower volume of blood/testing liquid mixture to be dispensed from blood collector into testing strip for an analyte meter or the like. The "double pop" phenomenon of the blood collector and blood sampler body disclosed in the '655 patent is graphically illustrated by the curve in FIG. 8 labeled "Prior Art". FIG. 8 plots the insertion force required to insert the blood collector into the sampler body versus the distance the sample collector is provided within the sampler body. More specifically, in this known example, the average extension is the distance the portion of the blood collector used to create a seal with the blood sampler passes the seal ring on the blood sampler body. The continuous line identified as "Prior Art" shows the presence of two peaks or apexes in the curve. The first peak occurs when the sealing portion of the blood collector is approximately 0.45 inches past the seal ring in the blood sampler body. At this point, approximately 2 Newtons of force is required to insert the blood collector. The second peak occurs when the sealing portion of the blood collector is approximately 0.45 inches past the seal ring of the blood sampler body. At this point, approximately 12 Newtons of force is required to insert the blood collector into the blood sampler body. However, it is the sharp drops or jumps in the curve immediately following the two peaks, i.e., at an average extension of approximately 0.50 and 0.64 inches, that represent the "double pop" sensation or the feedback felt by a user. The first jump or drop in the resistance force profile occurs at approximately 0.50 inches. Because of the premature drop in force required to insert the sealing portion of the blood collector into the blood sampler body, users are improperly led to believe that the blood collector is fully inserted into the sampler body. It is not until the second drop, at approximately 0.64 inches, that the blood collector is fully inserted into the blood sampler. This point represents the point at which no further force can cause the blood collector to be further inserted into the blood sampler.

Reducing or eliminating this sudden jump in the resistance force profile, and therefore the "double pop" sensation, could reduce or eliminate the likelihood of user error in using a blood sampler device. In this regard, a reduction or elimination of user error can increase the consistency in the volume of blood/testing liquid mixture to be dispensed from blood collector into testing strip. Such an increase in the volume of blood dispensed can facilitate more consistent and/or more accurate test results.

BRIEF SUMMARY OF THE INVENTION

It would therefore be beneficial to provide a device that overcomes this disadvantage by eliminating any jumps in the resistance force profile. The present invention relates generally to such liquid testing devices and, more particularly, to a blood sampler with an improved design.

According to one aspect of the disclosed embodiment, a blood sampler device includes a sampler body forming a hollow internal chamber with upper and lower openings. The sampler body includes a seal ring disposed adjacent to the upper opening. A first septum forms a seal over the upper opening. A second septum forms a seal over the lower opening. The blood sampler device also includes a blood collector adapted to be inserted into the sampler body. The blood collector includes a handle adapted to be gripped by a user. A seal surface extends around a circumference of the blood collector in a region adjacent to the handle. A pair of ribs is formed in a region adjacent to the seal surface. The ribs form a vent that is adapted to allow air to escape from the chamber as the blood collector is inserted into the sampler body. The seal surface engages the seal ring to form a substantially airtight seal upon complete insertion. The vent includes a top shoulder that forms a gradually sloped surface adapted to smooth a flow profile of air flowing over the gradually sloped surface.

In one embodiment of the device, the gradually sloped surface includes a substantially linear surface arranged at an angle with respect to the outer circumference of the seal surface.

According to another embodiment of this aspect of the device, the blood collector includes at least one bottom tip adapted to rupture the first septum. Alternatively, the blood collector may also include a capillary channel disposed within a lower portion thereof. The capillary channel may be adapted to hold a fluid therein.

According to another embodiment of the device, a plunger is disposed within a lower portion of the sampler body. The plunger may include at least one sharp portion adapted to rupture the second septum.

In accordance with another embodiment, a base is disposed in close proximity to a lower portion of the sampler body. The base may be adapted to receive a fluid.

In another embodiment, the pair of ribs each form an outer surface adapted to engage the seal ring as the blood collector is inserted into the sampler body while minimizing friction between the blood collector and the seal ring.

In accordance with another aspect of the presently disclosed invention, a blood sampler device includes a sampler body and a blood collector. The sampler body forms a hollow internal chamber with upper and lower opening and further includes a sealing device disposed adjacent to the upper opening. The blood collector is adapted to be inserted into the sampler body. The blood collector includes a seal surface that extends around a circumference of the blood collector; a pair of ribs formed in a region adjacent to the seal surface; and at least one vent formed between the pair of ribs. The vent is adapted to allow air to escape from the chamber as the blood collector is inserted into the sampler body. The vent includes a top shoulder that forms a gradually sloped surface adapted to smooth a flow profile of air flowing over the gradually sloped surface. When the blood collector is completely inserted into the sampler body, the seal surface engages the seal device to form a substantially airtight seal.

In accordance with one embodiment of this aspect, the gradually sloped surface of the shoulder includes a substantially linear surface that is arranged at an angle with respect to the outer circumference of the seal surface. The gradually sloped surface may also extend in a direction toward the lower opening.

In accordance with another embodiment of the invention, the pair of ribs each form an outer surface adapted to engage the seal device as the blood collector is inserted into the sampler body.

In accordance with another embodiment of this aspect of the invention, the blood collector further includes a capillary channel disposed within a lower portion thereof, which capillary channel is adapted to hold a fluid therein.

In accordance with another embodiment of this aspect of the invention, the blood sampler body may further include a base disposed in close proximity to a lower portion of the sampler body. The base is adapted to receive the fluid. Alternatively, the sampler body may further comprise a first septum forming a seal adjacent the upper opening, and a second septum forming a seal adjacent the lower opening. In still another alternative embodiment of the sampler body, the sampler body may further comprise at least one bottom tip adapted to rupture the first septum. There may also be a plunger disposed within a lower portion of the sampler body, the plunger including at least one sharp portion adapted to rupture the second septum.

In accordance with another embodiment of this aspect of the invention, the blood collector may further include a handle adapted to be gripped by a user and the seal surface may be positioned adjacent the handle.

In accordance with another embodiment of this aspect of the invention, the sealing device is a sealing ring extending around an inner surface of the sampler body.

In accordance with another aspect of the present invention, a device for preparing a fluid sample for use in a fluid analyte meter includes a sampler body and a blood collector. The sampler body forms a hollow internal chamber that has an inlet and an outlet and includes a sealing device within the sampler body. The blood collector is insertable into the inlet of the sampler body. The blood collector may have a first end and an opposed second end. A central axis may extend between the first and second ends along a central portion of the body. The sealing surface may extend around an outer surface of the blood collector. The vent may be disposed around the central axis of the blood collector and may include a shoulder having a gradual surface extending toward the central axis.

In another alternative embodiment of this aspect of the invention, the vent permits air to escape from within the sampler body as the blood collector is inserted into the sampler body.

In another alternative embodiment of this aspect of the invention, when the device is fully inserted into the sampler body, the shoulder is positioned closer to the central opposed outlet of the sampler body than the sealing device.

In another alternative embodiment of this aspect of the invention, the vent is adapted to smooth a flow profile of air flowing over the vent.

In another alternative embodiment of this aspect of the invention, the gradual surface is a sloped surface extending inwardly with respect to the sealing surface.

In still another embodiment of this aspect of the invention, the slope is constant.

In yet another embodiment of this aspect of the invention, the vent further includes a slot extending along a portion of the outer surface of the blood collector.

In another embodiment of this aspect of the invention, the blood collector further includes a pair of ribs adjacent the vent and the vent further comprises a recess between the pair of ribs.

In another embodiment of this aspect of the invention, the ribs extend along an outer surface of the blood collector.

In yet another embodiment of this aspect of the invention, the shoulder is rounded.

In another embodiment of this aspect of the invention, the gradual surface has a profile selected from the group consisting of a convex curve, a concave curve, and a compoundly angled surface.

In still another embodiment of this aspect, the sealing device is a seal ring extending around an inner circumference of the sampler body.

BRIEF DESCRIPTION OF THE DRAWINGS

Certain subject matter regarded as the invention is particularly pointed out and distinctly identified in the concluding portion of this specification. Organization and methods of operation of the present invention will now be described with reference to the appended drawings. It is appreciated that these drawings and their associated detailed descriptions depict only exemplary embodiments of the invention and are therefore not to be considered limiting of its scope.

FIG. 3A is an elevation view of the blood collector of FIGS. 2A, 2B;

FIG. 3B is an enlarged view of a portion of the blood collector of FIG. 3A;

DETAILED DESCRIPTION

In describing the preferred embodiments of the subject illustrated and to be described with respect to the drawings, specific terminology will be used for the sake of clarity. However, the invention is not intended to be limited to any specific terms used herein, and it is to be understood that each specific term includes all technical equivalents that operate in a similar manner to accomplish a similar purpose.

In a preferred embodiment, the present blood sampler device significantly reduces, if not eliminates, the "double pop" sensation associated with prior art devices. By significantly reducing or eliminating the sudden jump in the resistance force profile, and therefore the "double pop" sensation, the present device can further reduce, and preferably eliminate, the likelihood of user error and can therefore lead to greater consistency in the volume of blood dispensed, both of which can lead to more consistent and/or more accurate test results.

When a user inserts a blood collector into a sampler body of a blood sampler device, vents in the blood collector permit discharge of displaced air from the sampler body. At higher insertion speeds, vents in the blood collector become completely covered by the sampler body, and therefore closed to airflow, sooner than they would be if the blood collector were inserted more slowly. Moreover, known vents may not have configurations which are optimized to account for the volume of air being displaced. The insertion speed of the blood collector thus determines the amount of time available for air to escape from a liquid chamber within the sampler body via the vents, which directly affects the quantity of air that escapes (i.e., the vents remaining open for a longer time and, being optimally configured, allows a greater amount of air to escape from the liquid chamber). Accordingly, inserting the known blood collector more quickly may only allow a smaller quantity of air to escape, which can result in greater air pressurization within the liquid chamber.

In known devices, this relationship between the insertion speed of the blood collector and the quantity of air that escapes from the liquid chamber causes the resulting air pressurization within the liquid chamber to vary significantly based on the insertion speed of the blood collector. However, the blood collector of the blood sampler device provided herein is designed to smooth out the flow profile, or optimize the profile, of the air escaping from the liquid chamber and to provide vents with widened openings through which the air can escape. Therefore, the present design of the blood collector allows air to escape more smoothly and quickly than in known devices, which substantially reduces the impact of the insertion speed on the amount of air that escapes. Likewise, the present design also reduces the influence of the insertion speed of the blood collector on the air pressurization in the liquid chamber.

Figure 1A:
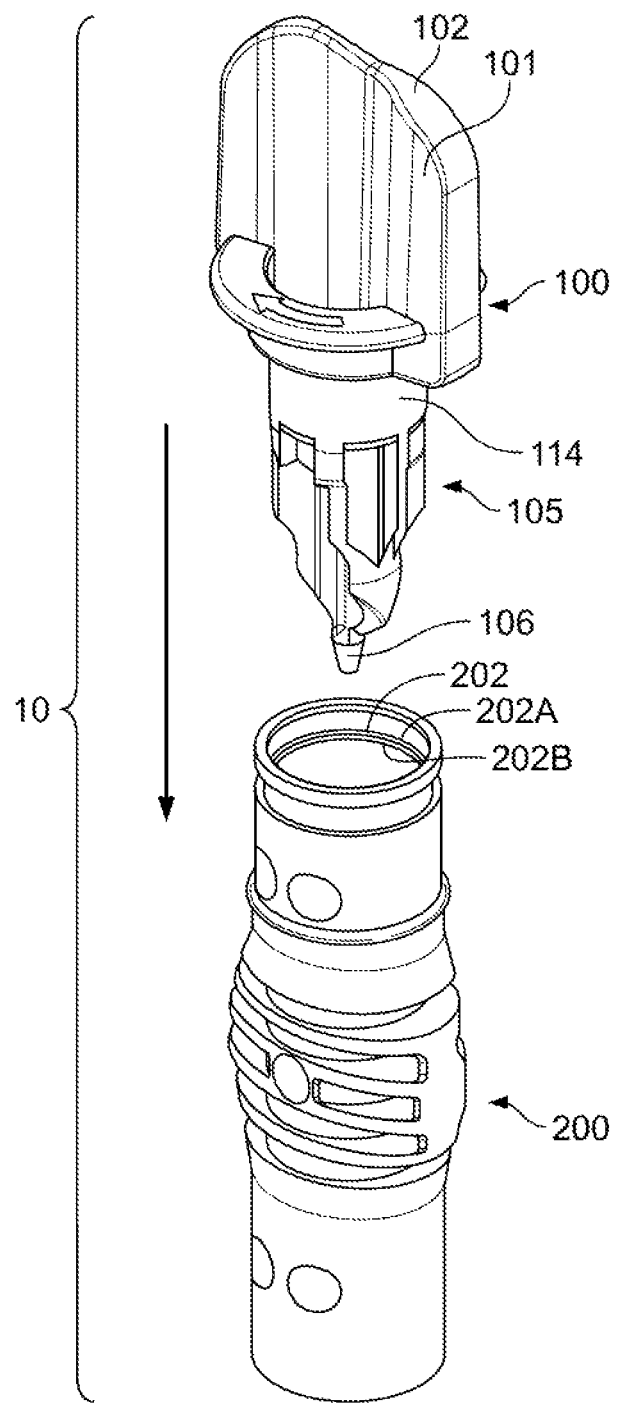
FIG. 1A is a perspective view of portions of a blood sampler device according to an exemplary embodiment of the present invention.

Referring to FIG. 1A, there is shown a blood collector 100 disposed above a sampler body 200 of a blood sampler device 10 according to one embodiment of the present invention. Blood collector 100 includes a handle 102 at an upper portion 101 thereof to be gripped by a user. A lower portion 105 of blood collector 100 is dimensioned to be inserted forcibly by the user into sampler body 200, which is generally shaped as a hollow cylinder. A liquid chamber 204 (see, e.g., FIG. 3A) is formed within sampler body 200, and contains a treatment solution, as well as air. The air in liquid chamber 204 becomes pressurized as blood collector 100 is inserted, and therefore naturally seeks an area of lower pressure. Blood collector 100 includes a set of vents 104A-104F (see FIG. 6) that each allow air to escape as liquid chamber 204 becomes pressurized during the insertion of lower portion 105 of blood collector 100 into the liquid chamber, and to thereby control the resulting pressurization in the liquid chamber. In the exemplary embodiment shown, blood collector 100 includes six vents 104A-104F (collectively vents 104); however, other embodiments may include a different number of vents 104.

Figure 1B:
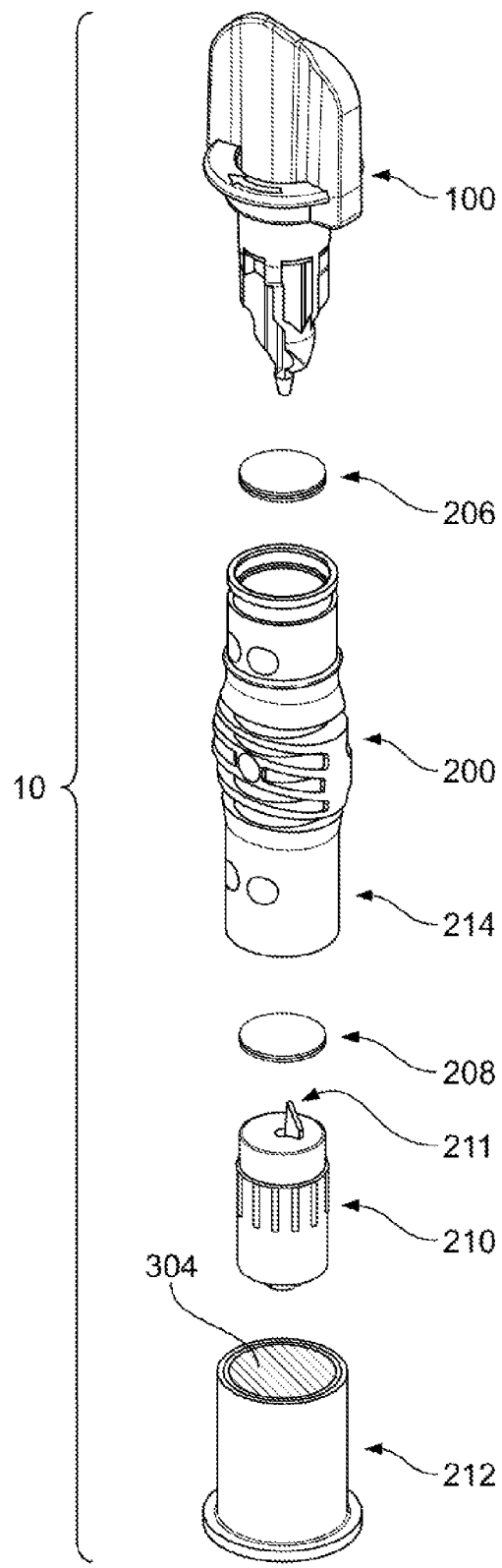
FIG. 1B is an exploded view of the portions of the blood sampler device of FIG. 1A.

FIG. 1B shows an exploded view of blood sampler device 10. Sampler body 200 includes a first septum 206 and a second septum 208 that respectively form seals over a top 205 and bottom 207 of liquid chamber 204 (see, e.g., FIG. 3A), the top 205 and bottom 207 being otherwise open. Preferably, first septum 206 and second septum 208 each include two foil layers. In other embodiments, first septum 206 and/or second septum 208 may include only one foil layer, or may include one or more additional foil layers and/or a polyester layer therebetween. Reducing the number of foil layers can reduce the amount of insertion force required to rupture first septum 206 and second septum 208. When blood sampler device 10 is in use, a plunger 210 is disposed within sampler body 200 below liquid chamber 204. A base 212 is also included, and is disposed within a lower portion 214 of sampler body 200. Plunger 210 is disposed at least partially within base 212, and includes a sharp upper portion 211 designed to rupture second septum 208, which causes the liquid or liquid mixture held within liquid chamber 204 to flow into plunger 210 and/or into base 212. The sharp upper portion may be configured as a blade, simple spike, or other piercing element.

Figure 2A:
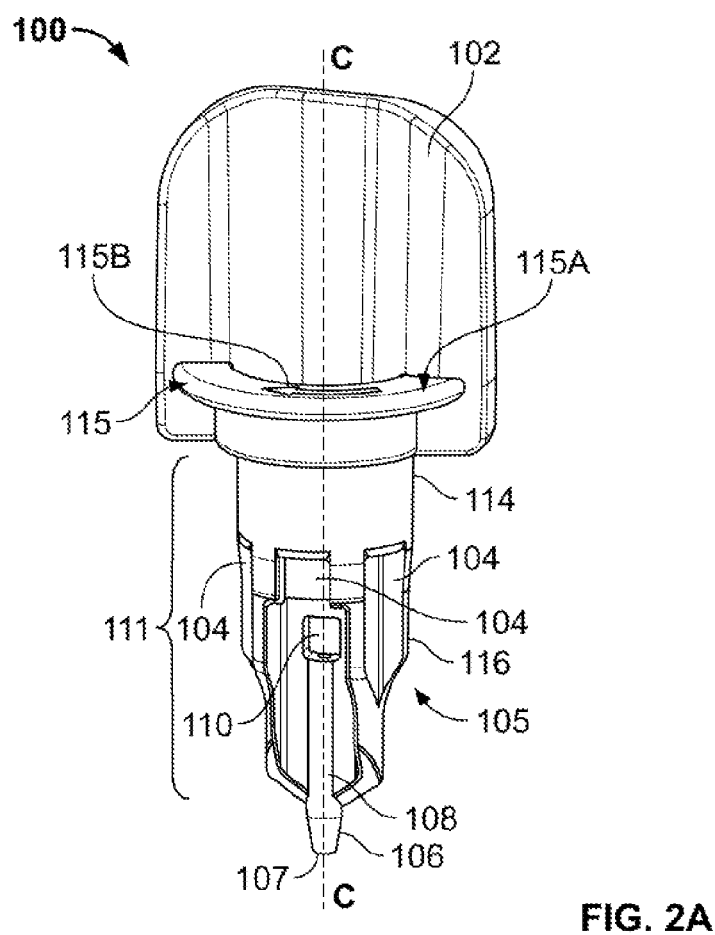
FIG. 2A is a perspective view of a blood collector of the blood sampler device of FIG. 1A.

FIG. 2A depicts a partially cut-away view of blood collector 100. As shown, blood collector includes a tip 106, a capillary channel 108 and vents 104. Bottom tip 106 is formed on lower portion 105 of blood collector 100. In one example, bottom tip 106 is formed from a substantially hard material, such as a suitable polymer, plastic, metal, or other appropriate material, and in the shape of a cone, point, or other piercing element. In some embodiments, bottom tip 106 may be substantially sharp and/or may include a relatively small surface area in comparison with first septum 206, as will be discussed below. The sharp shape or small surface area enables tip to more easily penetrate the septum 206. An opening 107 is formed adjacent the end of bottom tip 106 and provides an entrance into an internal capillary channel 108. Capillary channel 108 is formed as a substantially cylindrical tubular cavity, extending upwardly from opening 107 in bottom tip 106 to a stop junction 110. Stop junction 110 is an enlarged cavity portion of the capillary channel 108. In the exemplary embodiment shown, stop junction 110 has a substantially square cross-section. However, in other embodiments, stop junction 110 may include any other type of cross-section, such as substantially circular, rectangular, or another shape.

Figure 2B:
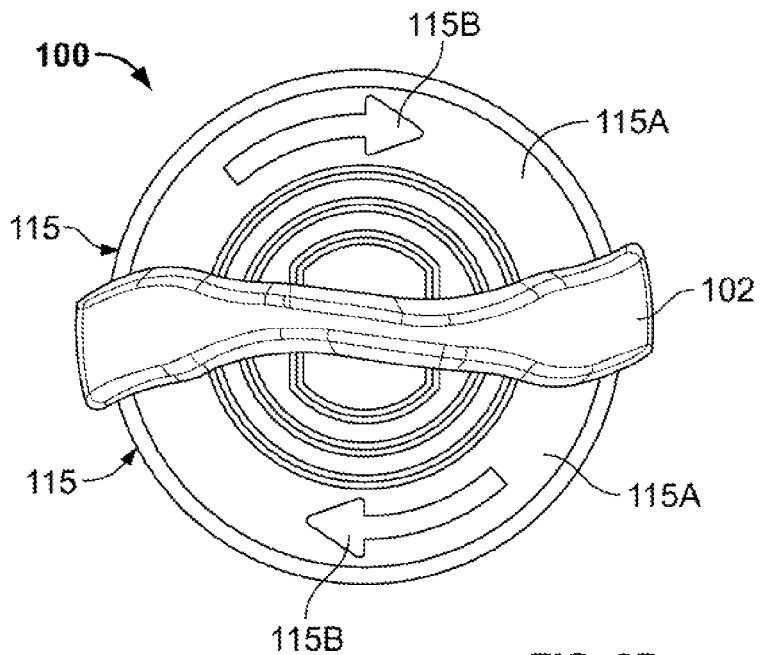
FIG. 2B is a top view of a blood collector of the blood sampler device of FIG. 1A.

With reference still to FIG. 2A, blood collector 100 may include one or more flanges 115 adjacent a lower end of handle 102. Flange 115 circumferentially extends around handle 102 providing one or more surfaces 115A on which a user may exert pressure while inserting blood collector 100 into sampler body 200 with reduced discomfort to the user. In some embodiments, flanges 115 may be widened in comparison with known devices. Although not required, flanges 115 may include one or more indicators 115B, such as arrows or another similar marking, to instruct a user to twist blood collector 100 in a particular direction while inserting blood collector 100 into sampler body 200. As best shown in FIG. 2B, handle 102 of blood collector 100 may be asymmetrically contoured to provide a user with a better grip of blood collector 100 when blood collector 100 is in use and inserted into the sampler body 200. The handle 102 configuration allows a user to easily twist the blood collector 100 when placed into sampler body 200. The ability to twist blood collector 100 during the insertion of blood collector 100 can aid in reducing the insertion force required to insert blood collector 100 into sampler body 200.

Referring to FIGS. 3A-3B, each vent 104 of the blood collector 100 is formed between a series of ribs 116A-116F (collectively "ribs 116") included on lower portion 105 of blood collector 100. As discussed in further detail below, ribs 116 each form an outer surface that is adapted to engage a seal ring 202 of sampler body 200 as blood collector 100 is inserted into sampler body 200. Upper portions 103A-103F of vents 104A-104F respectively include a set of shoulders 109A-109F (collectively "shoulders 109"). Shoulders 109A-109F, respectively, include gradually sloped surfaces 112A-112F (collectively "gradually sloped surfaces 112"). In the example shown, the shoulder extends toward the central axis C (FIG. 2A) of the blood collector.

FIG. 3B shows a close-up view of gradually sloped surfaces 112A, 112B, and 112F formed by shoulders 109A, 109B, and 109F, respectively. The gradually sloped surfaces 112 of shoulders 109 are designed to smooth out the flow profile of air flowing over shoulders 109 as the air leaves vents 104. Gradually sloped surfaces 112 also smooth the transition from vents 104 to a full seal surface 114, as discussed in further detail below. Gradually sloped surfaces 112 may be linear, or of constant slope, or may have a slope which gradually changes, such as by increasing along the height of the slope.

Figure 4:
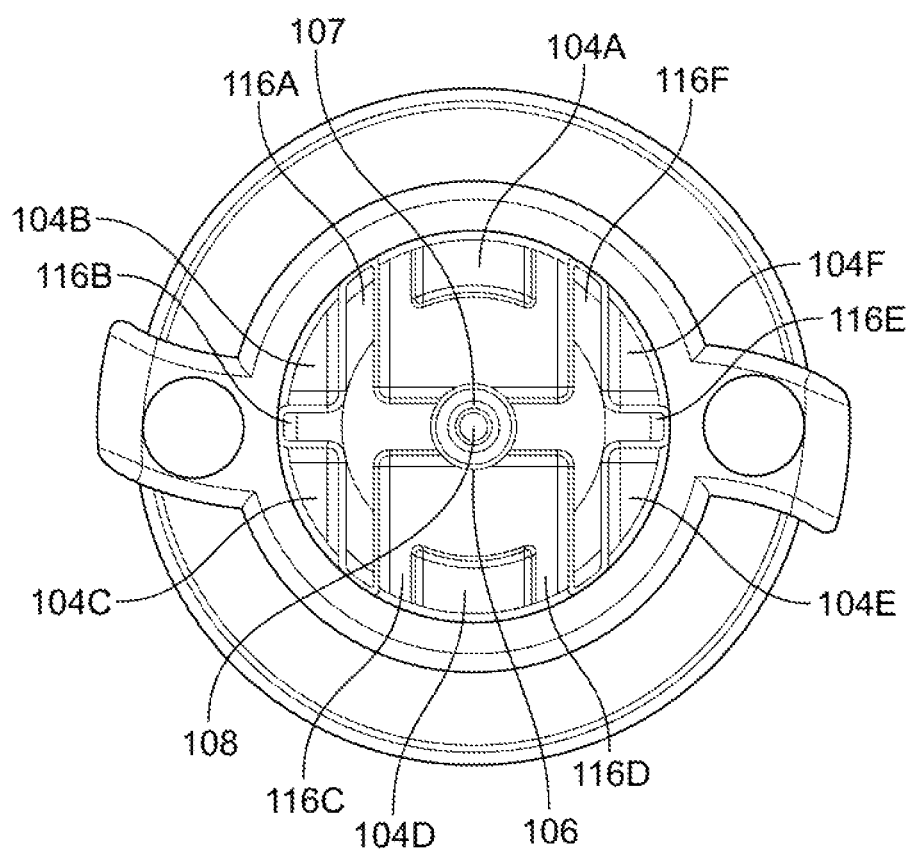
FIG. 4 is a bottom view of the blood collector of FIGS. 2A, 2B.

FIG. 4 is a bottom view of blood collector 100, and shows ribs 116A-116F included on lower portion 105 of blood collector 100. In the exemplary embodiment shown, ribs 116A-116F are formed by the same structure of blood collector 100 that forms vents 104A-104F. Ribs 116 are designed and arranged to engage seal ring 202 (see FIG. 1) disposed within sampler body 200 as a user inserts blood collector 100 into sampler body 200. The exemplary embodiment shown includes six ribs 116A-116F and six vents 104A-104F; however, other embodiments may include a different number of ribs and/or a different number of vents.

Figure 5A:
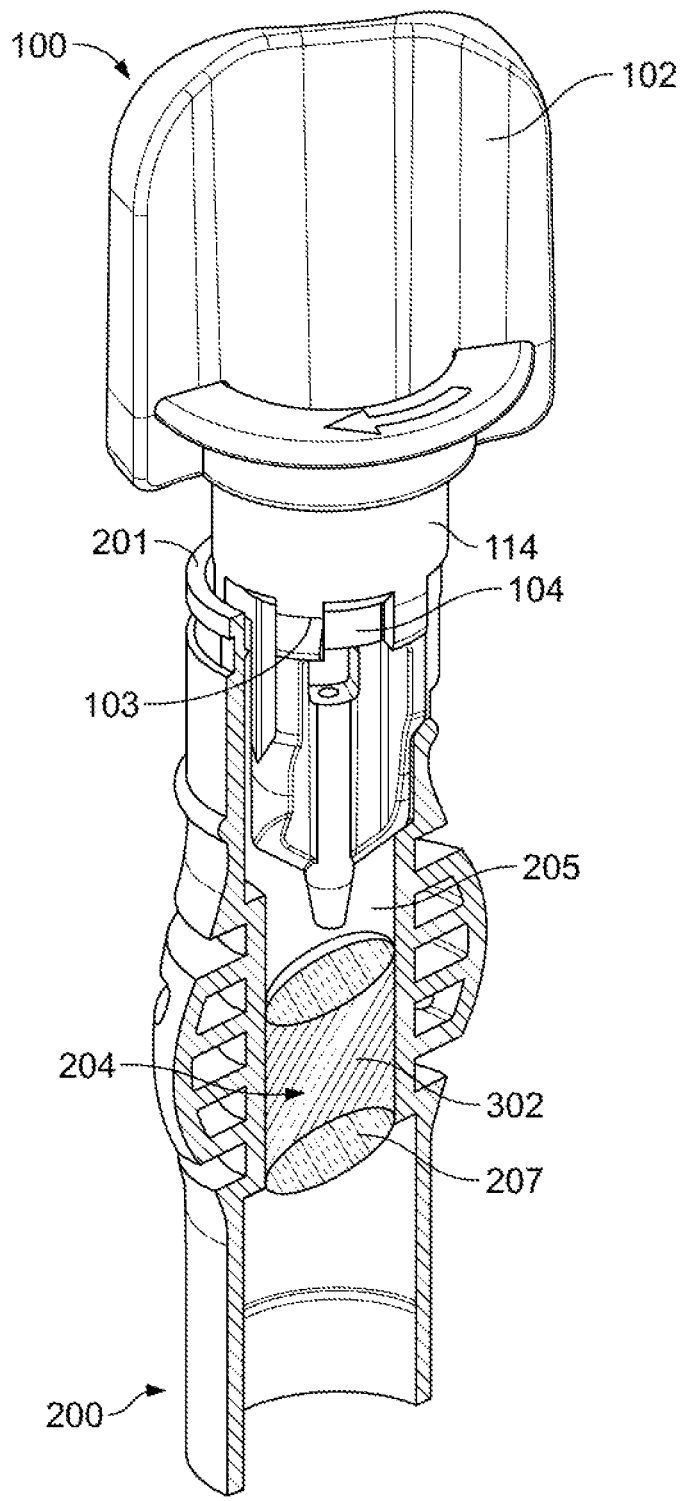
FIGS. 5A and 5B are cut-away perspective views of the blood collector partially inserted into the sampler body of the blood sampler device of FIG. 1A, including arrows indicating the flow of air from the blood sampler device in FIG. 5B.
Figures 5B, 6A:
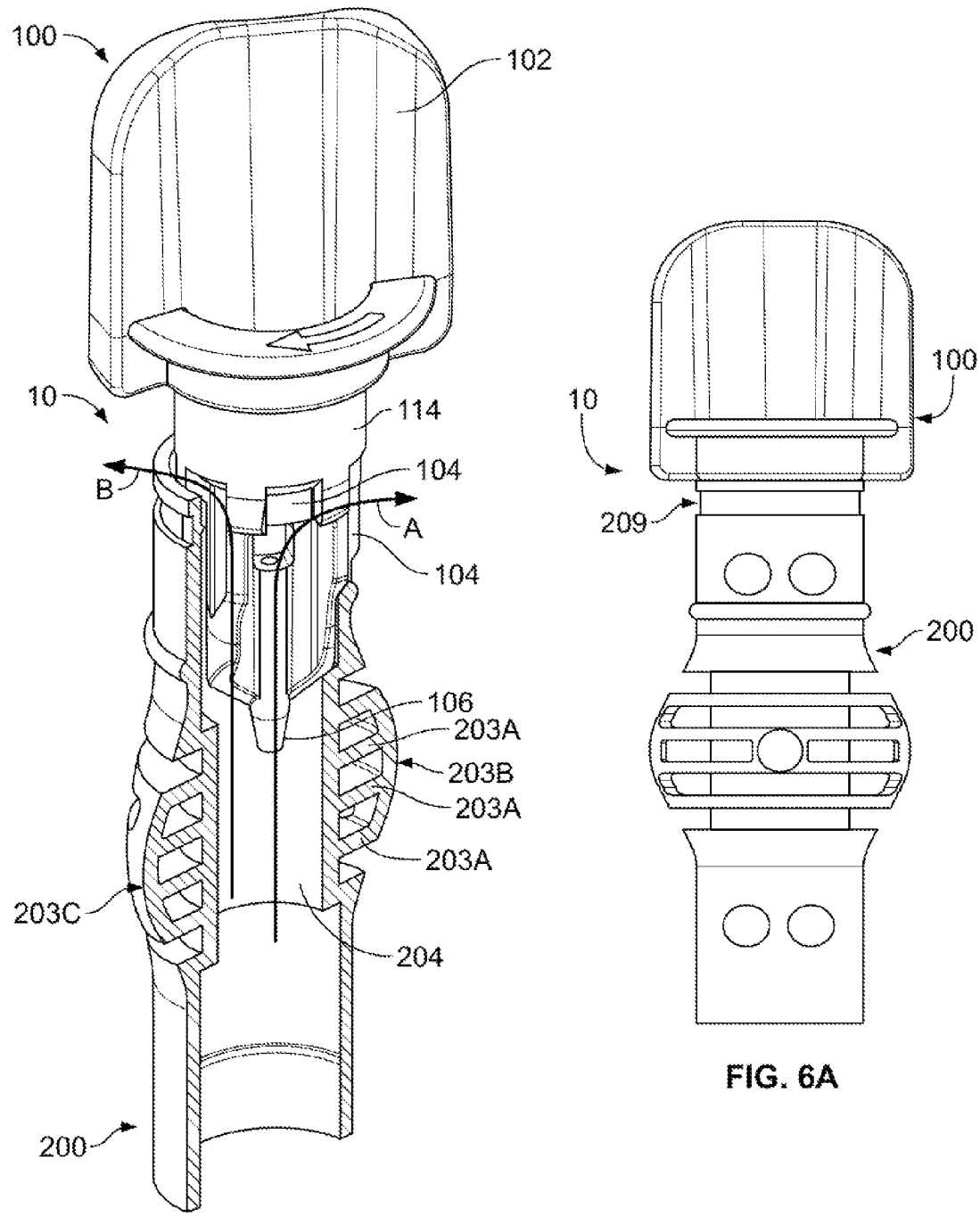
FIG. 6A is a front perspective view of the blood collector fully inserted into the sampler body of the blood sampler device of FIG. 1A.

Turning to sampler body 200, in one embodiment, as shown in FIGS. 1A and 5A-5B, sampler body 200 may include one or more grip fins 203A, along a portion of the outside thereof, to allow a user to grip sampler body 200 more easily. In the embodiment shown, grip fins 203A are arranged substantially horizontally and substantially parallel to one another, but may, in other embodiments, be oriented differently, such as at an angle with respect to a longitudinal axis of sampler body 200 and/or at an angle with respect to one another. The exemplary embodiment shown also includes two connecting fins 203B, 203C extending over the spaces between grip fins 203A. Other embodiments may include additional connecting fins or only one connecting fin. Connecting fins 203B, 203C may reduce the likelihood of multiple sampler bodies 200 becoming jammed with one another during manufacturing, such as by the grip fins 203A of a first sampler body 200 interlocking with the spaces formed between the grip fins 203A of a second sampler body 200. In the exemplary embodiment shown, two connecting fins 203B, 203C are shown. However, other embodiments may include only one connecting fin or may include more than two connecting fins. Additionally, although the exemplary embodiment shown depicts connecting fins 203B, 203C arranged substantially vertically, one or more of connecting fins 203B, 203C may, in other embodiments, be arranged at an angle. Other embodiments may also include connecting fins 203B, 203C extending over fewer than all of grip fins 203A.

When the blood sampler device 10 is in operation, blood collector 100 is held near a liquid such that the liquid is drawn by capillary effect into capillary channel 108 through opening 107. In one embodiment, the liquid is blood from an open puncture of a patient's skin. Stop junction 110 (FIG. 2A) is formed as a bore through lower portion 105 of blood collector 100. In this way, stop junction 110 functions to allow a predetermined amount of liquid to be collected and held in capillary channel 108.

FIGS. 5A-5B show blood sampler device 10 in an intermediate position during use, in which blood collector 100 is partially inserted into sampler body 200. Vents 104A-104F each respectively include an upper portion 103A-103F (collectively upper portions 103). In the partially inserted position shown in FIGS. 5A-5B, upper portions 103 of vents 104 of blood collector 100 are partially exposed above a top 201 of sampler body 200, such that at least some of the pressurized air in liquid chamber 204 is capable of escaping through vents 104. In the exemplary embodiment shown, upper portions 103 form a substantially rectangular opening, but may, in other embodiments, include a different shape, such as a square, curve, semi-circle, or other suitable shape. Arrows A-B in FIG. 5B represent the flow of air out of liquid chamber 204 via vents 104 during the pressurization of liquid chamber 204 that results from the insertion of blood collector 100 into sampler body 200.

Figure 6B:
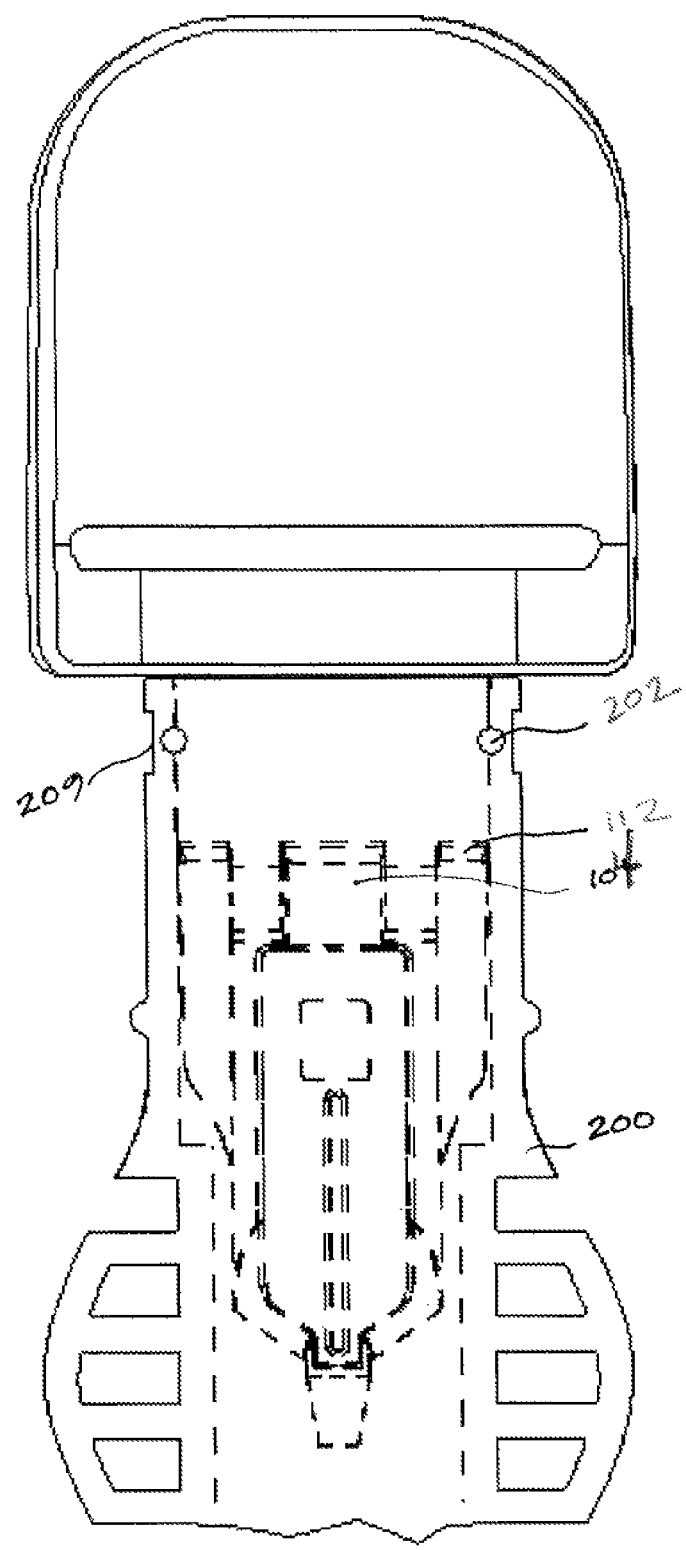
FIG. 6B is a front plan view of the blood collector fully inserted into the sampler body of the blood sampler device of FIG. 1A.

FIGS. 6A-6B depicts blood sampler device 10 at a stage of use subsequent to the stage depicted FIGS. 3A-3B, during which blood collector 100 is fully inserted into sampler body 200, such that vents 104, including upper portions 103, are completely covered by sampler body 200. Therefore, when blood collector 100 is fully inserted into sampler body 200, air can no longer escape from liquid chamber 204 through vents 104. With reference still to FIGS. 6A-6B, in the exemplary embodiment shown, sampler body 200 may include a recessed relief groove 209 around the outside of the top 201 of sampler body 200. Recessed relief groove 209 may reduce the insertion force required to insert blood collector 100 into sampler body 200. For example, relief groove 209 may reduce the required insertion force by allowing top 201 of sampler body 200 to temporarily deform from its natural size and shape as blood collector 100 is inserted. In this regard, sampler body 200 may be made from any suitably resilient material, for example, metals, plastics, polymers, other appropriate materials, and/or combinations thereof.

First septum 206 (see FIG. 1B) forms a seal over the top of liquid chamber 204, and is ruptured by bottom tip 106 when a user inserts blood collector 100 into sampler body 200. Rupturing may be caused by the bottom tip 106 being formed by a particular material; the shape of the tip; and/or if bottom tip 106 includes a relatively small surface area in comparison with first septum 206, such that the force with which blood collector 100 is inserted into sampler body 200 is concentrated on a relatively small surface area of first septum 206. Concentrating the insertion force on a relatively small surface area of first septum 206 would cause first septum 206 to rupture under less insertion force than would be required if the insertion force were distributed over a greater surface area.

As blood collector 100 is inserted further into sampler body 200, thus bringing bottom tip 106 further into liquid chamber 204, air within liquid chamber 204 becomes pressurized, which forces some of the air to escape through vents 104 in blood collector 100. With the improved design, this flow of air is smoothed to prevent over-pressurization of the liquid chamber. After blood collector 100 is fully inserted into sampler body 200 (see FIGS. 6A, 6B), a quantity of blood 300 (see FIG. 3A) held in capillary channel 108 is dispensed into liquid chamber 204 to mix with a treatment solution 302 (see FIG. 5A) contained therein. The resulting mixture is referred to herein as a test fluid 304. In an exemplary embodiment, a user may then shake blood sampler device 10 to facilitate the mixing of blood 300 with treatment solution 302.

Figure 7:
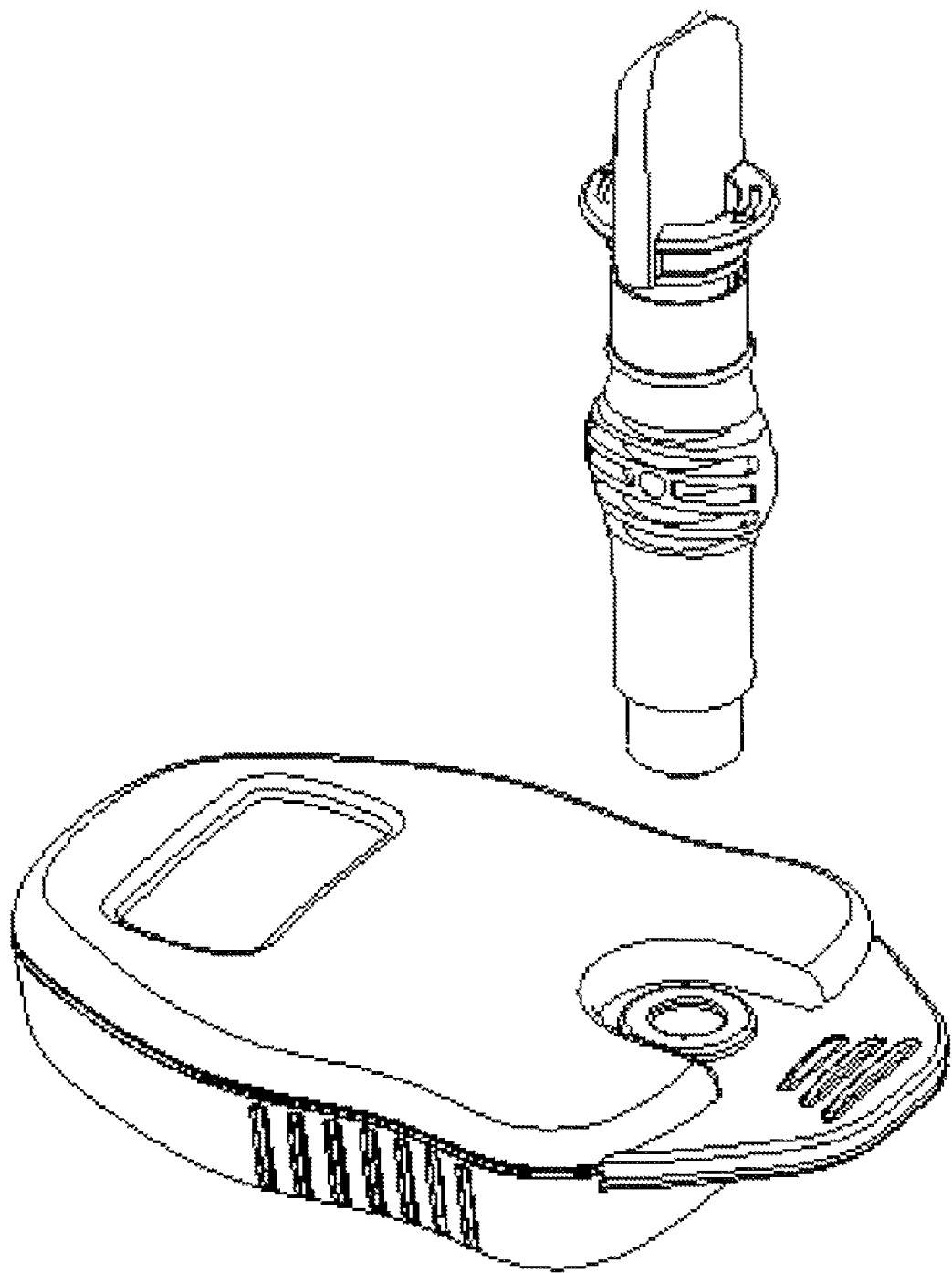
FIG. 7 is a perspective view of the blood sampler device of FIG. 1A and an analyte meter.

After blood 300 is discharged from capillary channel 108 into liquid chamber 204 to mix with treatment solution 302, plunger 210 is moved upward, such that sharp upper portion 211 ruptures second septum 208, causing test fluid 304 to be discharged from liquid chamber 204 of sampler body 200 into base 212. A fluid analyte meter is subsequently used to analyze test fluid 304. Device 10 may be designed so that fluid 304 is dispensed through a dispensing nozzle (not shown) into a test meter 400, as shown in FIG. 7. The accuracy of the analysis results is highly dependent on the volume of blood 300 dispensed from blood collector 100 into liquid chamber 204 to mix with treatment solution 302 and form the mixture of test fluid 304. Therefore, it is preferable for a user to operate blood sampler device 10 properly, such that an appropriate volume of blood 300 is dispensed from blood collector 100. Preferably, substantially all of the blood 300 held in capillary channel 108 is dispensed into liquid chamber 204, though acceptable results may also be possible when only a portion of the blood 300 is dispensed into liquid chamber 204.

When a user inserts blood collector 100 into sampler body 200 at a higher insertion speed, vents 104 become completely covered by sampler body 200, and therefore closed to airflow, sooner than they would be if blood collector 100 were inserted more slowly. The insertion speed of blood collector 100 thus determines the amount of time available for air to escape from liquid chamber 204 via vents 104, which directly affects the quantity of air that escapes (i.e., the vents remaining open for a longer time allows a greater amount of air to escape from the liquid chamber). Accordingly, inserting blood collector 100 more quickly allows a smaller quantity of air to escape, resulting in greater pressurization within liquid chamber 204.

In known devices, this relationship between the insertion speed of the blood collector and the quantity of air that escapes from the liquid chamber causes the resulting pressurization within the liquid chamber to vary significantly based on the insertion speed of the blood collector. However, the blood collector provided herein is designed to smooth out the flow profile of the air escaping from the liquid chamber through vents in the blood collector, and to provide vents with widened openings through which the air escapes. Therefore, the present design of the blood collector allows air to escape more quickly than in known devices, which substantially reduces the impact of the insertion speed on the amount of air that escapes. Likewise, the present design also reduces the influence of the insertion speed of the blood collector on the air pressurization in the liquid chamber.

In the exemplary embodiment shown, vents 104 are widened in comparison with the vents of known blood sampler devices. The increased width of vents 104 provides a larger opening than vents of known devices, which allows air to escape from liquid chamber 204 more quickly as compared to known devices. In this way, the exemplary embodiment shown makes the amount of air that escapes less dependent on the length of time for which vents 104 are exposed outside of sampler body 200. Thus, the speed with which a user inserts blood collector 100 into sampler body 200 has a less significant influence on the resulting amount of pressurization in liquid chamber 204. Accordingly, the design of vents 104 provided herein reduces the range of variation in the pressurization, providing greater consistency in the resulting pressurization.

The amount of pressurization within liquid chamber 204 directly affects the volume of blood/testing liquid mixture that is dispensed from sampler body to test strip, as higher pressures cause a greater amount of liquid to be dispensed. Therefore, controlling the amount of pressurization in liquid chamber 204 allows a proper volume of liquid mixture to be dispensed. This ultimately leads to more accurate fluid analyte testing results.

An upper region 118 of blood collector 100 forms a continuous circumferential seal surface 114 extending between vents 104 and handle 102. In upper region 118, the diameter of blood collector 100 may be greater than the diameter in the region of vents 104. Known devices often include an abrupt transition between these regions of different diameters, such as right angles protruding radially outwardly from the top of the vents. Such abrupt transitions can cause escaping air to change direction suddenly, thereby causing turbulence in the airflow. Turbulence causes faster-moving air to mix with the slower-moving air near the boundary layer, which slows down the overall speed of the escaping air across the flow profile. Slowing down this overall speed would reduce the amount of air that can escape, as compared to a flow profile with a faster overall speed. Therefore, when the air escapes at a slower overall speed, more air remains in liquid chamber 204, resulting in greater air pressurization within liquid chamber 204.

The exemplary embodiment shown includes shoulders 109 each forming a gradual lead-in formed on upper portions 103 of each vent 104. As best shown in FIGS. 3A-3B, each shoulder 109 of this exemplary embodiment forms a gradual surface 112 that is sloped inwardly with respect to seal surface 114 of blood collector 100 to provide a gradual transition between the larger diameter of seal surface 114 and the smaller diameter in the region of vents 104. In the exemplary embodiment shown, each gradual surface 112 includes a substantially flat, angled surface; however, in other embodiments, gradual surfaces 112 may include a different profile, such as a convex curve, a concave curve, a compoundly angled surface, or other suitable profile, or a combination thereof.

Gradual surfaces 112 guide the escaping air to change direction smoothly, which reduces, and preferably eliminates, turbulence. The general flow direction of the escaping air is represented by arrow C (see FIG. 3B). Reducing or eliminating turbulence allows the escaping air to maintain a higher overall speed across the flow profile than would be achieved with more turbulent flow. Accordingly, gradual surfaces 112 increase the quantity of air that can escape, which reduces the pressurization in liquid chamber 204. Therefore, the present design of shoulders 109 further reduces the influence of the insertion speed of blood collector 100 on the resulting amount of pressurization that occurs within liquid chamber 204.

The present device also reduces the resistance force profile felt by the user when inserting blood collector 100 into sampler body 200. To this end, blood collector 100 includes ribs 116 (see FIG. 4). Ribs 116 are designed and arranged to maximize the size of vents 104 while providing enough outer surface area to effectively engage seal ring 202 within sampler body 200 as blood collector 100 is inserted into sampler body 200. Seal ring 202 includes an upper edge 202A and a lower edge 202B.

Seal ring 202 acts like an O-ring, and facilitates the forming of a seal to prevent liquids or air from escaping from (or entering) liquid chamber 204. When blood collector 100 is fully inserted into sampler body 200, seal ring 202 engages seal surface 114 to form a seal. In one embodiment, seal ring 202 forms a substantially airtight seal with seal surface 114.

As blood collector 100 is inserted into sampler body 200, an outermost surface 111 of blood collector 100 engages seal ring 202, causing friction and thereby creating a resistance force profile felt by the user. The magnitude of the resistance force is directly proportional to the amount of surface area of blood collector 100 that contacts seal ring 202, which is directly related to the outer diameter of blood collector 100 in the regions of seal surface 114 and of ribs 116, and to the inner diameters of sampler body 200 and seal ring 202. Ribs 116 form a relatively small outer surface area in the region of vents 104, which reduces, and preferably minimizes, the resistance force when blood collector 100 is inserted partially within sampler body 200 such that ribs 116 engage seal ring 202.

After blood collector 100 is inserted into sampler body 200 far enough for ribs 116 to pass seal ring 202, seal ring 202 is suddenly engaged by seal surface 114 of blood collector 100. Surface 114 is continuous around the circumference of blood collector 100, and therefore forms a substantially greater outer surface area than ribs 116 form, the ribs 116 being separated by the recessed vents. Such a sudden, substantial increase in the amount of surface area contacting seal ring 202 may cause a sudden jump in the resistance force profile felt by the user, as the resistance force is directly proportional to the amount of surface area of blood collector 100 engaging seal ring 202. Gradual surfaces 112 formed on shoulders 109 of vents 104 greatly reduce, and preferably prevent, such a sudden jump in the resistance force profile. Because gradual surfaces 112 are angled inwardly with respect to the outer circumference of blood collector 100, gradual surfaces 112 contact seal ring 202 at an angle, rather than in a radial direction of seal ring 202, providing a smooth transition from the smaller outer surface area of ribs 116 to the significantly greater surface area of seal surface 114 contacting seal ring 202. This smooth transition avoids a sudden jump in the resistance force profile felt by the user while inserting blood collector 100 into sampler body 200, which, as discussed above, can lead to more consistent and/or more accurate test results.

Figure 8:
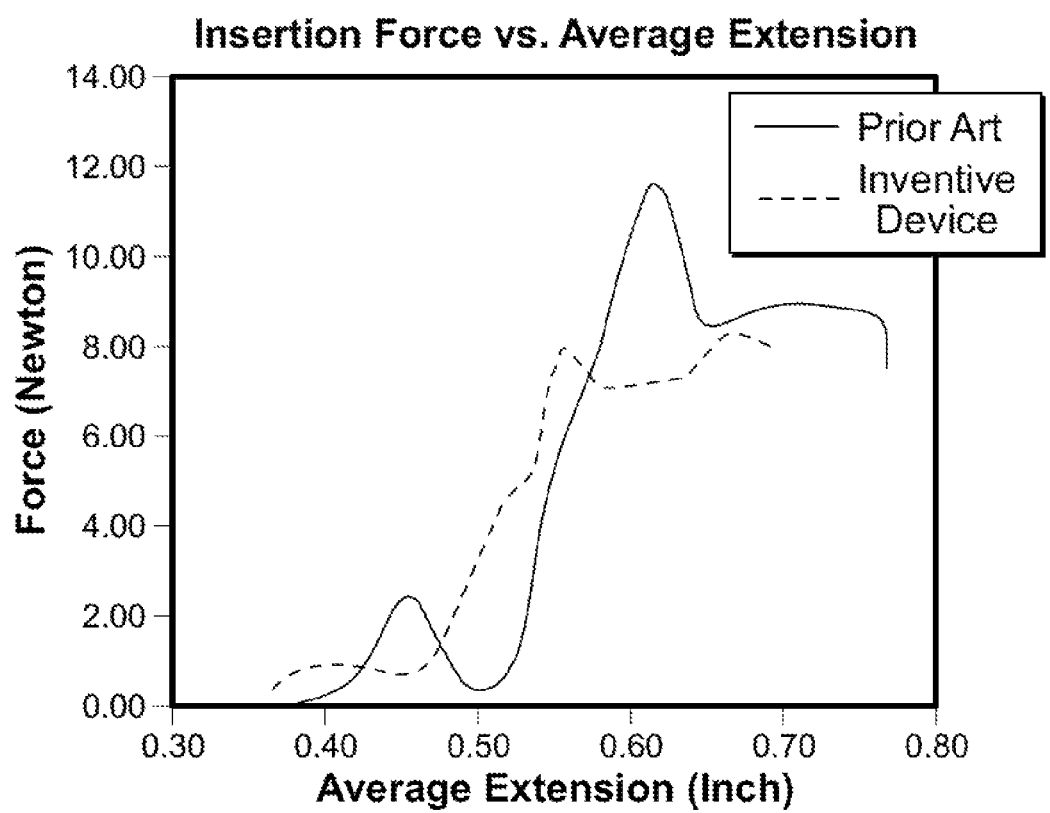
FIG. 8 is a plot of force profiles as a function of the insertion distance of the blood collector for a known blood sampler device and for the blood sampler device according to an exemplary embodiment of the present invention.

FIG. 8 compares the plot of the resistance force felt by the user, as a function of the insertion distance of the blood collector for an exemplary embodiment of the present device ("Inventive Device"), with an exemplary known device shown in the '655 patent ("Prior Art") (previously discussed). In the Inventive Device, the average extension is measured at the point at which the seal surface 114 passes the upper edge 202A of the seal ring on the sampler body 200. As shown in FIG. 8, the force profile for this exemplary embodiment is substantially smoother (i.e., more gradual) than the force profile for the exemplary known Prior Art device, and reaches an appreciably lower maximum force. Thus, a user using blood sampler device 10 according to this exemplary embodiment experiences a smoother and lower resistance force profile while inserting blood collector 100 into sampler body 200 than would be felt using a known device. For example, at an average extension of 0.50 inches, the resistance force profile for the Inventive Device has steadily increased to 4 Newtons, whereas the insertion force of the Prior Art device has dropped to approximately 1 Newton. The present design of the Inventive Device has eliminated the first jump or drop in the force resistance profile such that there is only one jump or drop in the force resistance profile, i.e., the final drop. This design thereby essentially eliminates the "double pop" sensation felt by a user. Thus, by reducing the force profile felt by the user during insertion of blood collector 100, the design of blood sampler device 10 leads to more accurate blood sampling test results.

Figure 9:
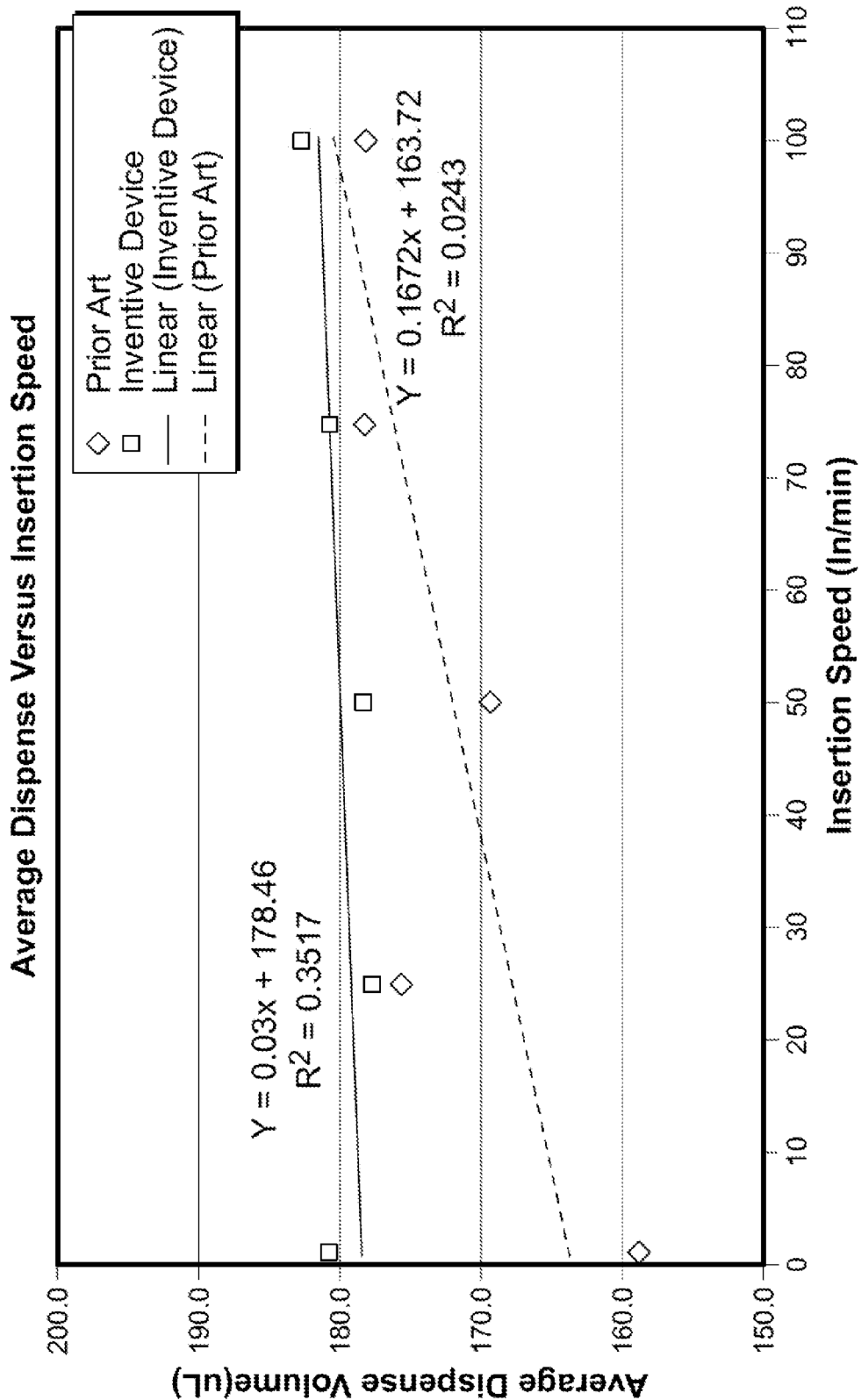
FIG. 9 is a plot of the dispense volume of blood as a function of the insertion speed of the blood collector for a known blood sampler device and for the blood sampler device according to an exemplary embodiment of the present invention.

FIG. 9 shows a graph of the average volume of blood dispensed plotted as a function of the insertion speed of a blood collector for the exemplary embodiment of the present device, i.e., the Inventive Device, as compared with the exemplary known device disclosed in the '655 patent, i.e., the Prior Art. As shown in this graph, the slope of the Prior Art line increases in relation to the increasing insertion speed. This indicates that the average amount of material dispensed from the Prior Art is a function of the insertion speed. For example, at a rate of 100 inches per minute, approximately 175 μl are dispensed, as compared to only 165 μl of sample dispensed when the blood collector is inserted into the sample body at a lower rate of 1 inch/minute. In this regard, the slope shows that more sample is dispensed when the blood collector is inserted into the sample body at a faster rate.

The slope of the line shown for the Inventive Device illustrates that the average dispense volume for the Inventive Device is less sensitive to changes in the insertion speed than the average dispense volume for the Prior Art. For example, the average dispense volume of the Inventive Device is more consistent between different insertion speeds than for known prior art devices, making the present device less prone to user error or manipulation.

Variation in the volume of liquid mixture dispensed, as well as insufficiently low dispense volumes, can compromise the results of the analyses performed on the test fluid dispensed by a blood sampler device. Thus, greater consistency in dispense volumes leads to more accurate test results. Accordingly, by reducing the resistance force profile, and therefore reducing or eliminating the likelihood of a user prematurely stopping the insertion of blood collector 100, the blood sampler device 10 of the above-described exemplary embodiment provides increased accuracy in blood sampling test results, as compared to known devices.

In the exemplary embodiment shown, blood collector 100 and sampler body 200 are shown and described as having generally circular cross-sections; however, in other embodiments, blood collector 100 and sampler body 200 may include other cross-sectional shapes. Additionally, blood collector 100 and sampler body 200 may each be made from a variety of materials, such as polymers, plastics, metals, other suitable materials known in the art, or suitable combinations thereof.

It is to be understood that the present invention is not limited to use with blood samples. Instead, any other fluid that is to be analyzed in any type of fluid analysis meter may be substituted. As such, the present invention encompasses operation with various fluid samples, including body fluid samples that include analytes such as prostate specific antigen, lipids, creatinine, microalbumin, etc.

Preferably, the meter with which the present device is used is a HbA1c meter; however, it is to be understood that the present invention is not so limited. Instead, any form of analyte meter (for measuring one or more analytes) is compatible with the present invention. Thus, the present invention may entail, but is not limited to, mixing a blood sample with a dilution buffer. For example, the present invention may also be useful for mixing blood with other substances, and may also be used in conjunction with other devices. The functioning of an exemplary meter was described in commonly owned U.S. Pat. Nos. 5,837,546; 5,945,345 and 5,580,794, each of which is incorporated by reference herein in their entirety. It is to be understood, however, that the present invention may also be used with any suitable fluid analysis meter, or even with a simple containment vessel (e.g., for preparing a sample for deposition in a well, such that it can be analyzed in the future).

In optional aspects of the invention, blood sampler device 10 may be used with either: a single use test meter (examples of which were described in U.S. Pat. Nos. 5,837,546; 5,945,345; and 5,580,794), or a multi-use cartridge system (an example of which was described in U.S. Provisional Application No. 60/550,410), the disclosures of which are incorporated herein in their entirety.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended aspects of the invention.

The invention claimed is:

1. A blood sampler device, comprising:
    a sampler body forming a hollow internal chamber with upper and lower openings, the sampler body including a sealing device disposed adjacent to the upper opening; and
    a blood collector adapted to be inserted into the sampler body, the blood collector including
        a first end and an opposed second end;
        an opening adjacent the second end;
        a seal surface extending around a circumference of the blood collector;
        a pair of ribs formed in a region adjacent to the seal surface; and
        at least one vent formed between the pair of ribs, the at least one vent in the region adjacent to the seal surface, the ribs forming the at least one vent, the vent being adapted to allow air to escape from the chamber as the blood collector is inserted into the sampler body, and the vent comprising a top shoulder extending inwardly from the seal surface in a direction toward the opening, the vent forming a gradually sloped surface adapted to smooth a flow profile of air flowing over the gradually sloped surface,
    wherein the seal surface engages the seal device to form a substantially airtight seal upon complete insertion of the blood collector into the sampler body.

2. The blood sampler device according to claim 1, wherein the gradually sloped surface comprises a substantially linear surface arranged at an angle with respect to the outer circumference of the seal surface.

3. The blood sampler device according to claim 1, wherein the gradually sloped surface extends in a direction toward the lower opening.

4. The blood sampler device according to claim 1, wherein the pair of ribs each form an outer surface adapted to engage the sealing device as the blood collector is inserted into the sampler body.

5. The blood sampler device according to claim 1, wherein the blood collector further comprises a capillary channel disposed within a lower portion thereof, the capillary channel being adapted to hold a fluid therein.

6. The blood sampler device according to claim 5, the blood sampler device further comprising a base disposed in close proximity to a lower portion of the sampler body, the base being adapted to receive the fluid.

7. The blood sampler device according to claim 1, wherein the sampler body further comprises a first septum forming a seal adjacent the upper opening, and a second septum forming a seal adjacent the lower opening.

8. The blood sampler device according to claim 7, wherein the sampler body further comprises at least one bottom tip adapted to rupture the first septum.

9. The blood sampler device according to claim 8, the sampler body further comprising a plunger disposed within a lower portion of the sampler body, the plunger including at least one sharp portion adapted to rupture the second septum.

10. The blood sampler device according to claim 1, the blood collector further comprising a handle adapted to be gripped by a user and the seal surface being positioned adjacent the handle.

11. The blood sampler device of claim 1, wherein the sealing device is a sealing ring extending around an inner surface of the sampler body.

12. A device for preparing a fluid sample for use in a fluid analyte meter, comprising:
    a sampler body forming a hollow internal chamber, the sampler body having an inlet, an outlet, and a sealing device within the sampler body; and
    a blood collector being insertable into the inlet of the sampler body, the blood collector having a first end and an opposed second end, a central axis extending between the first and second ends along a central portion of the body, a sealing surface extending around an outer surface of the blood collector, a vent disposed around the central axis of the blood collector, the vent including a shoulder having a gradually sloped surface extending from the seal surface toward the central axis, and a pair of ribs adjacent the vent, the vent formed between the pair of ribs, the ribs forming the at least one vent.

13. The device of claim 12, wherein the vent permits air to escape from within the sampler body as the blood collector is inserted into the sampler body.

14. The device of claim 12, wherein when the blood collector is fully inserted into the sampler body, the shoulder is positioned closer to the central opposed outlet of the sampler body than the sealing device.

15. The device of claim 12, wherein the vent is adapted to smooth a flow profile of air flowing over the vent.

16. The device of claim 15, wherein the gradual surface is a sloped surface extending inwardly with respect to the sealing surface.

17. The device of claim 16, wherein the slope is constant.

18. The device of claim 12, wherein the vent further comprises a slot extending along a portion of the outer surface of the blood collector.

19. The device of claim 12, wherein the blood collector further comprises a recess between the pair of ribs.

20. The device of claim 19, wherein the ribs extend along an outer surface of the blood collector.

21. The device of claim 12, wherein the shoulder is rounded.

22. The device of claim 12, wherein the gradual surface has a profile selected from the group consisting of a convex curve, a concave curve, and a compoundly angled surface.

23. The device of claim 12, wherein the sealing device is a seal ring extending around an inner circumference of the sampler body.

* * * * *